United States Patent [19]
Jaynes et al.

[11] Patent Number: 5,597,946
[45] Date of Patent: Jan. 28, 1997

[54] METHOD FOR INTRODUCTION OF DISEASE AND PEST RESISTANCE INTO PLANTS AND NOVEL GENES INCORPORATED INTO PLANTS WHICH CODE THEREFOR

[75] Inventors: Jesse M. Jaynes; Kenneth S. Derrick, both of Baton Rouge, La.

[73] Assignee: Board of Supervisors of Louisiana State University and Agricultural and Mechanical College, Baton Rouge, La.

[21] Appl. No.: 444,762

[22] Filed: May 19, 1995

Related U.S. Application Data

[63] Continuation of Ser. No. 152,939, Nov. 15, 1993, abandoned, which is a continuation of Ser. No. 993,448, Dec. 16, 1992, abandoned, which is a continuation of Ser. No. 845,348, Mar. 4, 1992, abandoned, which is a continuation of Ser. No. 373,623, Jun. 29, 1989, abandoned, which is a continuation of Ser. No. 889,225, Jul. 25, 1986, abandoned.

[51] Int. Cl.$^6$ .............................. A01H 5/00; C12N 15/56; C12N 15/82; C12N 15/84; C12N 15/12
[52] U.S. Cl. ................... 800/205; 435/69.1; 435/70.1; 435/172.3; 435/200; 435/252.2; 435/320.1; 536/23.5
[58] Field of Search ....................... 435/69.1, 70.1, 435/172.3, 200, 252.2, 320.1; 800/205; 536/23.5

[56] References Cited

U.S. PATENT DOCUMENTS

| | | | |
|---|---|---|---|
| 3,911,110 | 10/1975 | Smirnoff | 424/93 |
| 4,109,018 | 8/1978 | Thompson | 426/62 |
| 4,355,104 | 10/1982 | Hultmark et al. | 435/70 |
| 4,520,016 | 5/1985 | Hultmark et al. | 514/12 |
| 4,579,821 | 4/1986 | Palmiter et al. | 435/172.3 |
| 4,643,988 | 2/1987 | Segrest et al. | 514/12 |
| 4,704,362 | 11/1987 | Itakura et al. | 435/253 |
| 4,962,028 | 10/1990 | Bedbrook et al. | 435/172.3 |

FOREIGN PATENT DOCUMENTS

| | | |
|---|---|---|
| 0142924 | 5/1985 | European Pat. Off. . |
| 0043075 | 6/1982 | Germany . |
| 0157351 | 10/1985 | Germany . |
| 0182278 | 5/1986 | Germany . |
| 1311375 | 3/1973 | United Kingdom . |
| 063949 | 11/1982 | United Kingdom . |
| 117600 | 9/1984 | United Kingdom . |
| 140556 | 5/1985 | United Kingdom . |
| 145338 | 6/1985 | United Kingdom . |
| 0184288 | 6/1986 | United Kingdom . |
| WO86/04356 | 7/1986 | WIPO . |
| WO88/00976 | 2/1988 | WIPO . |
| WO89/00199 | 1/1989 | WIPO . |

OTHER PUBLICATIONS

Anderson, Lucy, *J. Cell Sci.*, "Protein Synthesis and Uptake by Isolated Cecropia Oocytes", 1971, 8:735–750.

Andreu, D., et al., *Proc. Natl. Acad. Sci.*, "Solid-phase synthesis of Cecropin A and Related Peptides", 1983, 80:6475–6479.

Andreu, D., et al., *Biochemistry*, "N-Terminal Analogues of Cecropin A: Synthesis, Antibacterial Activity, and Conformational Properties", 1985, 24:1683–1688.

Barton, K. A., *Science*, "Prospects in Plane Genetic Engineering", vol. 219, 11 Feb. 1983, pp. 671–676.

Beachy, R. *Genetic Tech News*, "Virus Genes Might Protect Plants From Disease", 1985, 8:4–5.

Bernheimer, A. W., et al., *Biochimica et Biophysica Acta*, "Interactions between Membranes and Cytolytic Peptides", 1986, 86:123–141.

Bessler, W. G., *Biochemical and Biophysical Research Communications*, "Interaction of Membrane Modifying Peptide Antibiotics from *Trichoderma viride* with Leukocytes", 1979, 87:99–105.

Blasi, Udo, *Gen. Virol.*, "Influence of C-terminal Modifications of ΦX174 Lysis Gene E on its Lysis-inducing Properties", 1985, 66:1209–1213.

Boller, Thomas, *UCLA Symp. Mol. Cell. Biol.*, Newser, "Induction of Hydrolases as a Defense Reaction Against Pathogens", 1985 (Cell. Mol. Biol. Plant Stress).

Boman, H. G., *Developmental and Comparative Immunology*, "On the Primary Structures of Lysozyme, Cecropins and Attacins from *Hyalophora cecropia*", 1985, 9:551–558.

Bowman, John E., *American Potato Journal*, "Resistance to *Pseudomonas solancearum* in Potato: Infectivity Titrations in Relation to Multiplication and Spread of the Pathogen", 1982, 59:155–164.

Brillinger, G. U., *Arch. Microbiol*, "Metabolic Products of Microorganisms 181*. Chitin Synthase from Fungi, a Test Model for Substances with Insecticidal Properties", 1979, 121:71–74.

Buckley, K. J., *Mol. Gen. Genet*, "Lytic Activity Localized to Membranespanning Region of ΦX174 E Protein", 1986, 204:120–125.

*Central Patents Index*, Basic Abstracts Journal, Section C, AGDOC, Dec. 1977, abstract 91378, Derwent Publications Ltd., (Japan) Plywood Techn. 29–11–1977 "Making Lumber Insect Repellent by Permeating with Aqueous Solution Containing Amylase, and Rinsing with Water.

*Central Patents Index*, Basic Abstracts Journal, Section C, AGDOC, Jul. 1979, abstract 53721, Derwent Publications (Mitsui Petrochem Ind. K.K.) 12–06–1979 "Antimicrobial Enyme prepared by Culturing Bacillus Bacteria".

Chilton, Mary–Dell, *Scientific American*, "A Vector for Introducing New Genes into Plants", 1983, 248:50–59.

(List continued on next page.)

*Primary Examiner*—David T. Fox

[57] ABSTRACT

A method of inhibiting pathogenic conditions of plants including viral, bacterial, and fungal infections and insert infestations by expressing into the plant genome genes encoding for a polypeptide inhibitor or inhibitor precursor of the pathogenic condition which inhibitor or precursor is selected from complementary oligonucleotides for blocking viral transcription or translation produced in vivo, one or more proteins derived from the humoral response to bacterial infection of the Hyalophora, an antifungal plasmid or a chitin integument disruption chitinase enzyme. Novel microbes, polypetides, and compositions containing amino acid sequences are disclosed.

7 Claims, No Drawings

OTHER PUBLICATIONS

Coleman, Jack, *Cell*, "The use of RNAs Complementary to Specific mRNAs to Regulate the Expression of Individual Bacterial Genes", 1984, 37:429–436.

Comai, L., *Plasmid*, "A New Technique for Genetic Engineering of *Agrobacterium* Ti Plasmid", 1983 10:21–30.

Comai, L., *Nature*, "Expression in Plants of a Mutant AroA Gene from *Salmonella typhimurium* Confers Tolerance to Glyphosate", 1985, 317:741–744.

Daum, Gunter, *Biochem. and Biophys. Res. Comm.*, "Reversible Activation and Inactivation of Phosphofructokinase from *Ascaris suum* by the Action of tissue-Homologous Protein Phosphorylating and Dephosphorylating Enzymes, 1986 139:215–221.

Deshpande, M. V., *Journal of Scientific and Industrial Research*, "Enzymatic Degradation of Chitin & Its Biological Applications", 1986, 45:273–281.

Doel, M. T., *Nucleic Acids Research*, "The Expression in *E. coli* of Synthetic Repeating Polymeric Genes coding for Poly(L–aspartyl–L–phenylalanine)", 1980, 8:4575–4593.

Drummond, M., *Nature*, "Launching Genes Across Phylogentic Barriers", 1983, 303:198–199.

Drutz, David, *Basic & Clinical Immunology*, "Immunity & Infection", 1984, 197–201.

Engstrom, A., *The EMBO Journal*, "Insect Immunity. The Primary Structure of the Antibacterial Protein Attacin F and its Relation to Two Native Attacins from *Hyalophora cecropia*", 1984, 3:2065–2070.

Engstrom, A., *The EMBO Journal*, "Amino Acid and cDNA Sequences of Lysozyme from *Hyalophora cecropia*", 1985, 4:2119–2122.

Fingl, Edward, *The Pharmacological Basis of Therapeutics*, "General Principles" Chapter 1, 1975. pp. 1–2.

Fischhoff, David A., *Bio/Technology*, "Insect Tolerant Transgenic Tomato Plants", 1987, 5:807–813.

Fraley, R. T., *Proc. Nat. Acad. Sci. USA*, "Expression of Bacterial Genes in Plant Cells", 80:4803–4807, Aug. 1983.

Freeman, J. P., *Plant & Cell Physical*, "A Comparison of Methods for Plasmid Delivery into Plant Protoplasts", 1984, 25(8):1353–1365.

French, E. R., *Phytopatholoqy*, "Resistance to *Pseudomonas solanacearum* in Potato: Specificity and Temperature Sensitivity", 1982, 72:1408–1412.

Fromm, Michael, *Proc. Natl. Acada. Sci.*, "Expression of Genes Transferred into Monocot and Dicot Plant Cells by Electroporation", 1985, 82:5824–5828.

Fromm, Michael, *Nature*, "Stable Transformation of Maize after Gene Transfer of Electroporation", 1986, 319:791–793.

Fuchs, R. L., *Applied and Environmental Microbiology*, "Cloning of a *Serratia marcescens* Gene Encoding Chitinase", 1986, 51:504–509.

Garcia, Lopez, *Biochem Genetics*, 106:190368d "Production of Lysozyme of *Streptococcus pneumonia* in *Escherichia coli* by Recombinant DNA Technology", 1986.

Garrett, Jinnie, *Mol. Gen. Genet.* "Cell Lysis by Induction of Cloned Lambda Lysis Genes", 1981, 182:326–331.

Gaynor, John J., *Chemical Abstracts*, "Defense Genes in Bean Seedlings: Induction of Chitinase by Ethylene", 1986, 104:183450e.

Gelehrter, Thomas D., *Biochem. and Biophys. Res. Comm.*, "Stimulation of Monovalent Ion Fluxes and DNA Synthesis in 3T3 Cells by Melittin and Vasopressin is not mediated by Phospholipid Deacylation", 1980, 97:716–724.

Gibson, Bradford W., *The Journal of Biological Chemistry*, "Novel Peptide Fragments Originating from $PGL^a$ and the Caerulein and Xenopsin Precursors from Xenopus laevis", 1986, 261:5341–5349.

Gilboa, Eli, *BioTechniques*, "Transfer and Expression by Cloned Genes Using Retroviral Vectors", 1986, 4:504–512.

Goodman, Robert M., *Science*, "Gene Transfer in Crop Improvement", 1987, 236:48–54.

Goy, P., *Agro. Division Report*, "Spectrum of Activity of 1 Synthetic Cecropin: In Vitro and In Vivo Tests", 12 F Report 89013xx, 1989.

Hashimoto, H., *Appl. Microbiol Biotechnol*, "A Novel Method for Transformation of Intact Yeast Cells by Electroinjection of Plasmid DNA", (1985) 21:336–339.

Hibi, T., *J. Gen. Virol.*, "High Efficiency Electro–transfection of Tobacco Mesophyll Protoplasts with Tobacco Mosaic Virus RNA", 1986, 67:2037–2042.

Horsch, Robert B., *Science*, "Inheritance of Functional Foreign Genes in Plants", 1984, 223:496–498.

Horwitz, Marc, *Mammalian Hormones*, "Genetic Improvement of Chitinase Production by Serratia marcescens", 1985, 102:216038R.

Hultmark, D., *Eur. J. Biochem.*, "Insect Immunity. Purification and Properties of Three Inducible Bactericidal Proteins from Hemolymph of Immunized Pupae of *Hyalophora cecropia*", 1980, 106:7–16.

Hultmark, D. *Eur. J. Biochem.*, "Insect Immunity. Isolation and Structure of Cecropin D Four Minor Antibacterial Components from Cecropia Pupae", 1982, 127:207–217.

Hultmark, D., *The EMBO Journal*, "Insect Immunity. Attacins, a Family of Antibacterial Proteins from *Hyalophora cecropia*", 1983, 2:571–576.

Iizuka, C., *Chemical Abstracts*, vol. 83, No. 17, 145:143033n, Oct. 1975 "Herbicides".

Isamu, H. *Chemical Abstracts*, "Aricine as a Bactericide and Fungicide", vol. 97, p. 290, abstract 97:87036r, 1982.

Izant, J., *Cell*, "Inhibition of Thymidine Kinase Gene Expression by Anti–Sense RNA: A Molecular Approach to Genetic Analysis", 1984, 36:1007–1015.

Jaynes, J. M., *Appl. Microbiol. Biotechnol*, "Construction and Expression of Synthetic DNA Fragments Coding for Polypeptides with Elevated Levels of Essential Amino Acids", 1985, 21:200–205.

Jaynes, J. M., *J. Cell Biochem.*, "Integration and Expression of Viroid cDNAs in Plant Cells", 1986, (10 Part C) p. 40.

Jaynes, J. M., *Trend Biotechnol*, "Plant Protein Improvement by Genetic Engineering: Use of Synthetic Genes", 1986, 4(12):314–320.

Jones, Jonathon, *Journal of Cellular Biochemistry*, "Engineering Bacterial Chitinase Genes for Crop Protection", Abstract J. 30, 1986.

Kado, C. I., *Phytopathogenetic Prokaryotes*, "Prospectus for Genetic Engineering in Agriculture", vol. 2, pp. 303–325, 1982.

Kangas, T., *Applied and Environmental Microbiology*, "Expression of a Proline–Enriched Protein in *Escherichia coli*, 1982, 43:629–635.

Kemp J. D., *Chemical Abstracts*, "Transfer of a Functional Gene via the Ti Plasmid", vol. 101, No. 3, Jul. 1984, pp. 176–177.

Kockum, K., *The EMBO Journal*, "Insect Immunity. Isolation and Sequence of Two cDNA Clones Corresponding to Acidic and Basic Attacins from *Hyalophora cecropia*", 1984, 3:2071–2075.

Krens, F. A., *Nature*, "*In vitro* Transformation of Plant Protoplasts with Ti-plasmid DNA", 1982, 296:72–74.

Langridge, W., *Plant Cell Reports*, "Electric Field Mediated Stable Transformation of Carrot Protoplasts with Naked DNA", 1985, 4:355–359.

Lee, J. Y., *The EMBO Journal*, "Insect Immunity. Isolation of cDNA Clones Corresponding to Attacins and Immune Protein P4 from *Hyalophora cecropia*" 1983, 2:577–581.

Loesch–Fries, L., UCLA Symp. *Molec. Cell Biol.*, "Cloning of Alfalfa Mosaic Virus Coat Protein Gene and Anti–sense RNA into a Binary Vector and their Express in Transformed Tobacco Tissue", 1986, p. 41.

Lorz, Horst, *Mol. Gen. Genet*, "Gene Transfer to Cereal Cells Mediated by Protoplast Transformation", 1985, 199:178–182.

Matthias, P., *Chemical Abstracts*, "Transient Expression of the Chicken Lysozyme Gene after Transfer into Human Cells", 1983, 98:12350a.

Merrifield, R. B., *Biochemistry*, "Synthesis of the Antibacterial Peptide Cecropin A(1–33)", 1982, 21:5020–5031.

Miyada, C. Garrett, *J. Bacteriol.*, "Five Mutations in the Promoter Region of the araBAD Operon of *Escherichia coli* B/r", 1983, 156: 765–772.

Molano, Jesus, *The Journal of Biological Chemistry*, "An Endochitinase from Wheat Germ", 1979, 254:4901–4907.

Monreal, J., *Canadian Journal of Microbiology*, vol. 15, 1969, (Ottawa); "The Chitinase of Serratia marcescens", 689–696.

Murai, N., *Chemical Abstracts*, "T–DNA of pTi–15955 from *Agrobacterium tumefaciens* is Transcribed into a Minimum of Seven Polyadenylated RNA's in a Sunflower Crown Gall Tumor", 96:17513h, 1982.

Nakai, T., *Chemical Abstracts*, "Synthesis of Self–defense Substance Produced by Silkworm, Lepidopteran, and Related Peptides", 106:214351w, 1986.

Nicolson, G., *The Journal of Cell Biology*, "Ultrastructural Localization of Lectin–Binding Sites on the Zonae Pellucidae and Plasma Membranes of Mammalian Eggs", 1975, 66:263–274.

Nitesche, W., *Theoretical and Applied Genetics*, "Chitinase as a Possible Resistance Factor for Higher Plants," vol. 65, No. 2, 1983.

Norrander, Jan M., *Jornal of Biotechnology*, "Manipulation and Expression of the Maize Zein Storage Proteins in *Escherichia coli*", 1985, 2:157–175.

Okada, K., *Plant Cell Physical*, "Introduction of Functional RNA into Plant Protoplasts by Electroporation", 1986, 27:619–626.

Okada, Masayuki, *Biochem. J.*, "Ionophore Activity of Sarcotoxin I, a Bactericidal Protein of *Sarcophaga peregrina*", 1985, 229:453–458.

Ou–Lee, T., *Botany*, "Expression of a Foreign Gene Linked to Either a plant–virus or a Drosophila Promoter, after Electroproation of Rice, Wheat, and Sorphum", 1986, 83:6815–6819.

Palukaitis, P., *Plant–Microbe Interactions*, "A Model to Explain the Cross–Protection Phenomenon Shown by Plant Viruses and Viroids", 1984 pp. 420–429.

Pownall, H. J., *Biochem. and Biophys. Res. Comm.*, "The Helical Hydrophobic Moment Avoids Prolines in Phospholipid–binding Proteins", 1986, 139:202–208.

Potrykus, I., *Mol. Gen. Genet.*, "Direct Gene Transfer to Cells of a Graminaceous Monocot", 1985, 199:183–188.

Ream, L. W., *Science*, "Crown Gall Disease and Prospects for Genetic Manipulation of Plants", vol. 218, pp. 854–859, 26 Nov. 1982.

Ream, L. W., *Proc. Nat. Acad. Sci. USA*, "Multiple Mutations in the T Region of the *Agrobacterium tumefaciens* Tumor–inducing Plasmid", vol. 80 pp. 1660–1664, Mar. 1983.

Rennell, Dale, *Virology*, "Phage P22 Lysis Genese: Nucleotide Sequences and Functional Relationships with T4 and v Genes", 1985, 143:280–289.

Sawazaki, T., *Chemical Abstracts*, "Enzymic fungicides", vol. 87, p. 160, abstract 87:79669c, 1977.

Shah, D., *Science*, "Engineering Herbicide Tolerance in Transgenic Plants", 1986, 233:478–481.

Shiba, T., *Chemical Abstracts*, "Antimicrobial Peptides from Silkworm Hemolymph", 104:230430k, 1985.

Shillito, R. D., *Biotechnology*, "High Efficiency Direct Gene Transfer to Plants", 1985, 3:1099–1103.

Soto–Gil, R., "Cloning of Vibrio harveyi Chitinase and Chitoblast Genes in *Escherichia coli*," 1984, 209–223.

Steiner, H., *Nature*, "Sequence and Specificity of two Antibacterial Proteins Involved in Insect Immunity", 1981, 292:246–248.

Uchimiya, H., *Mol. Gen. Genet.*, "Expression of a Foreign Gene in Callus Derived from DNA–treated Protoplats of Rice (Oryza sativa L.), 1986, 204:204–207.

Vaeck, M., *UCLA Symp. Mol. Cell. Biol.*, Newser, v. 48, Molecular Strategies for Crop Protection, "Engineering of Insect Resistance Plants Using a *B. Thuringiensis* Gene", 1986.

Van Hofsten, P., *Proc. Natl. Acad. Sci. USA*, "Molecular Cloning, cDNA Sequencing, and Chemical Synthesis of Cecropin B from Hyalophora cecropia", 1985, 82:2240–2243.

Vayda, Michael, *The Molecular and Cellular Biology of the Potato*, Chap. 15, "Enhancing Bacterial and Fungal Disease Resistance in Plants: Application to Potato", Destefano–Beltran et al., pp. 205–232.

White, A., *Principles of Biochemistry*, 6th ed., 1978, p. 708.

Wortman, A. T., *App. and Environt'l Microbiol*, "Chitinase Determinants of *Vibrio vulnificus:* Gene cloning and Applications of a Chitinase Probe", 1986, 52:142–145.

Wyatt, G. M., et al, "Potato Research", vol. 24, 1981, pp. 315–329.

Simons, R. W., et al, "Cell", vol. 34, Sep. 1983, pp. 673–682.

Pestka, S., et al, "Proceedings of the National Academy of Science U.S.A.", vol. 81, Dec. 1984, pp. 7525–7528.

Melton, D. A., "Proceedings of the National Academy of Science U.S.A.", vol. 82, Jan. 1985, pp. 144–148.

Werneke, J. M., et al, "Gene", vol. 38, 1985, pp. 73-84.

METHOD FOR INTRODUCTION OF DISEASE AND PEST RESISTANCE INTO PLANTS AND NOVEL GENES INCORPORATED INTO PLANTS WHICH CODE THEREFOR

This application is a continuation of application Ser. No. 08/152,939, filed Nov. 15, 1993, now abandoned; which is a continuation of application Ser. No. 07/993,448, filed Dec. 16, 1992, now abandoned ; which is a continuation of application Ser. No. 07/845,348, filed Mar. 4, 1992, now abandoned; which is a continuation of application Ser. No. 07/373,623, filed Jun. 29, 1989, now abandoned; which is a continuation of application Ser. No. 06/889,225, filed Jul. 25, 1986, now abandoned;the entire disclosure of each of which are incorporated by reference.

BACKGROUND OF THE INVENTION

This invention relates to a method for protecting plants from both disease and pests by means of genetic engineering to incorporate into the plant antagonistic agents or inhibitors for the infectious or harmful conditions which result. More specifically, plants suffer pathogenic conditions commonly known as diseases caused by virus, bacteria and fungus. Further, pests, such as various kinds of insects, cause untold damage to plants. The present invention provides a method for incorporating into the plant itself the means with which to deal with such pathogenic conditions.

Development of plant biology began in the early 1940s when experiments were being carried out to determine the biological principle causing formation of crown gall tumors. The tumor-inducing principle was shown to be a bacterial plasmid from the infective organism *Agrobacterium tumefaciens*. This plasmid has been characterized in exquisite biochemical detail utilizing the currently available techniques of recombinant DNA technology. The mode of operation for infection was the discovery that the bacterium elicits its response by actually inserting a small fragment of the bacterial plasmid into the plant nucleus where it becomes incorporated and functions as a plant gene. This discovery opened the door to using Agrobacterium and their plasmids as vehicles to carry foreign DNA to the plant nucleus. There are, however, limitations to the application of these techniques and they include: (1) susceptibility to infection with the Agrobacterium plasmid and (2) available tissue culture technology for regeneration of the transformed plants. These limitation have meant that, to date, there are no successful reports on genetic engineering of cereals because of the inability of Agrobacterium to infect cereal plants.

The plant genes, like all other genes, are simply strings of nucleic acid bases. The function of synthetic genes within the plant can be to produce a gene product which has its own intrinsic value or to produce an intermediate gene product, such as mRNA, that plays a regulatory role within the plant cell. Synthetic genes are most useable when the technical capability does not exist to isolate and purify genes from natural organisms. Both purified and synthetic genes may be used in conferring protection to plants against disease or pests. An example of the use of synthetic genes to confer resistance to viruses and viroids in plants comes through the use of the coevolution of many viruses with the plant hosts. Plants and animals have evolved very precise and elegant mechanisms which allow the regulated expression of their genes. Viruses by co-evolution have exploited and continue to exploit the eukaryotic cell of a plant by mimicking the general structure of the plant genes. Often, the end result of this for the plant is disease. While plants and animals are prisoners of their own evolution, so are viruses since they are dependent upon the plant and animal system of gene regulation and expression to synthesize and translate their own genes into the plant. This dependency is considered the key to control of viral disease. It has recently been found that bacteria regulate expression of some genes in a rather novel way. Under conditions where the cell would repress the biosynthesis of a particular protein, an additional level of control is exerted. This newly discovered type of gene control is called "micRNA" control and stands for "mRNA-interfering complementary RNA". This micRNA or "antisense" RNA is complementary to the 5' end of the gene and when it is produced has the ultimate effect of reducing the amount of messenger RNA (mRNA) by annealing to it, thus removing it from normal protein synthesis.

Viroids are single-stranded ribonucleic acid (RNA) of a few hundred nucleotides. They are the smallest self-replicating structures known and represent the lowest form of life. They are the causative agents of a number of plant diseases and elicit mild to lethal responses in a range of plants depending on the fine structure of the viroid and the susceptibility of the plant genotype. In the case of viroids, the logic is to inhibit the replication of the disease-causing molecule. Viroids are infective pieces of nucleic acid and do not have a protein component like viruses. Using methodology similar to viruses, we have the opportunity of blocking the nucleic acid replication (called transcription).

Many plants contain genes that confer virus resistance and, in some cases, resistance is due to a single dominant gene while, in other cases, the resistance is genetically more complex, i.e., requiring a number of genes to confer resistance. While it is presently practically impossible to identify, isolate and purify these resistance genes and, in fact, the chromosomes which carry these genes cannot even be located, utilizing the in vivo-produced antisense fragments, it may be possible to attain virus and viroid resistance by the insertion of a single synthetic gene which ultimately would produce an RNA complementary to specific regions of the viral genome and would play a role in the disruption of replication or translation of the virus. This complementary or antisense gene would be specific for a particular viral pathogen. Plants endowed with a number of these antisense genes would protect them from a variety of viral diseases, such as the symptoms observed in a viral disease of a potato.

In contrast to the use of one or more synthetic genes for protection of plants against viral disease, bacterial protection employs the known response of an insect to bacterial infection to confer resistance to bacterial disease. The pupae of Hyalophora (a type of silk moth) respond to bacterial infection by the synthesis of mRNAs which culminate in the production of about 15 to 20 new proteins. Lysozyme, the antibacterial protein found in egg white and human tears, and two other classes of antibacterial peptides, called cecropins and attacins, have been purified from these newly synthesized proteins. Lysozyme has been shown to be effective in limiting bacterial growth. When lysozyme was placed on a small paper dish in two concentrations, after an agar plate was seeded with plant pathenogenic bacteria, the lysozyme inhibitory zone was quite clear.

These proteins have a rather broad spectrum activity in that they are effective on many different types of bacteria. Thus, the insects have evolved a rather successful and novel means to fight bacterial infections. Although a traditional immunologist would think this system lacks specificity, the insect has a rather potent arsenal of at least three different bacterial proteins which may work in different ways to actively seek to destroy the bacterial pathogen. Thus, the invading bacteria is presented with a formidable challenge which would be very difficult to circumvent. While a bacterial pathogen may be naturally resistant to one, it is highly improbable that it would be resistant to all three toxins. Although determination of the exact mode of action of the protein toxins is required, they are quite prokaryote specific and appear to be benign to eukaryotic cells. Incorporation of the proteins derived from humoral response An Hyalophora are an attractive genetic system for protecting plants from bacterial disease which causes significant economic loss. As an example, the main diseases in potato are bacterial soft rot and bacterial wilt caused by *Erwiria carotovora* and *Pseudomona solanacearum*, respectively. These diseases are primarily responsible for limiting the growth of potatoes in many areas of Asia, Africa, South and Central America. The introduction of genes encoding for these antibacterial proteins into crop plants may revolutionize the protection of plants from bacterial-produced disease.

In a manner analogous to the antibacterial-protein producing insect, it has been found that some bacteria are natural repositories which contain genes encoding for proteins effective against fungi. The biochemical analysis of these compounds and the ultimate molecular characterization of genes encoding the synthesis of these natural antifungal agents could be of great importance in limiting the scope and severity of fungal disease in crop plants. It is believed that from 1845 to 1860 the fungal disease of the potato caused by *Phytophthora infetans* or Late Blight caused the Irish potato famine in which one million people died of starvation and one and a half million people immigrated to North America because of the decimation of the potato crop caused by this fungal pest.

Control of insect pests which cause tremendous losses of food and fiber derived from plants directly attributed to the insects and as a vector for the infection and spread of other plant pathogens requires increasing a plants tolerance to insect damage. Such increased tolerance would be of significant economic value. One method for protecting plants from insect damage is the use of natural insecticides such as a protein isolated from *Bacillus thuringiensis* which forms a high molecular weight crystal in the bacteria which is toxic to the larvae of a number of lepidopteral insects. However, it is believed that the insects would develop an immunity to the toxin within a few generations. Thus, other possibilities are being considered. One of the most promising is the use of an enzyme called chitinase as a natural insecticide. Chitinase is an enzyme produced in bacteria and the gene which encodes it has been isolated. An insect exoskeleton and gut are composed of chitin and it has been shown that any disruption of the chitin integument will result in the insect contracting an infection from the natural environment with death ensuing after a very short period of time. Inserting the enzyme-encoding gene for chitinase into the plant will provide a potent chitin-dissolving enzyme within the plant which will limit the extent of damage wrought by insects and secondarily limit the spread of other plant diseases which use insects as a vector.

SUMMARY OF THE INVENTION

In a broad aspect this invention provides a method of inhibiting a pathogenic plant condition which method comprises expressing into the plant genome an inhibitor for said condition derived by ligating from a natural or synthesized DNA source, a gene encoding for one or more polypeptide inhibitors or inhibitor precursors for said condition, inserting said gene into a plant vector and inserting said plant vector into a plant to be protected from the pathogenic plant condition.

More specifically, the present invention provides a method of inhibiting a pathogenic plant condition selected from viral infection, bacterial infection, fungal infection or insect infestation in a plant, said method comprising expressing into the plant genome one or more genes which encode for a polypeptide inhibitor or inhibitor precursor of said pathogenic condition, which inhibitor or precursor is selected from (a) a complementary oligonucleotide for blocking viral transcription or translation produced in vivo, (b) one or more proteins derived from the humoral response to bacterial infection of the Hyalophora, (c) an antifungal plasmid, and (d) a chitin integument disruption chitinase enzyme whereby such disruption results in subsequent infection from the environment of an insect feeding on said plant, said expressing being carried out by random ligation of a plasmid containing said inhibitor or precursor encoding gene, uptake of the inhibitor containing plasmid into *Escherchia coli* having a Hind III 17 fragment of T-DNA incorporated therein, introducing into an Agrobacterium strain carrying an unmodified R1 plasmid such that culturing with the plant genome results in said T-DNA containing the passenger (synthetic) DNA being incorporated into the plant genome and can be regenerated therewith to have an inhibiting effect for the pathogenic condition.

An alternative method of expressing the gene encoding for one or more polypeptide inhibitors or inhibitor precursors includes the ligation of such gene and insertion thereof into a plant vector identified as pMON237.

A more specific method of inhibiting or preventing virus production in plants ordinarily susceptible to said virus, which method comprises the expression into the plant gene of a complementary oligonucleotide for blocking the translation of said virus.

An additional aspect of the invention is a method of inhibiting or preventing bacterial disease in plants which includes expression of one or more genes encoding for one or more proteins derived from the humoral response to bacterial infection of the Hyalophora into the genome of a plant susceptible to bacterial infection.

A still further feature of the present invention includes a method of inhibiting fungal infections of plants ordinarily susceptible thereto, which method comprises expression of genes encoding for bacterially-derived proteins effective to inhibit growth of fungi.

A still further aspect of this invention provides a method for inhibiting damage to economically important crop or fiber plants from larvae of lepidopterans, which method comprises expressing the genes which code for chitinase enzyme into said crop or fiber plants such that upon ingestion by said larvae the chitinase enzyme disrupts the chitin integument of the larvae whereby such disruption results in subsequent infection, from external environmental sources.

DETAILED DESCRIPTION OF PREFERRED EMBODIMENTS

The method provided by the present invention provides an inhibitor for a number of adverse plant conditions, including bacterial infections, viral infections, fungal infections, and insect infestations. Initially, the method for inhibiting plant disease, particularly plant disease caused by bacterial infections, is considered. Bacterial infections are known to cause an antibacterial response in certain insects. As indicated above, the pupae of Hvalophora synthesize mRNA's which result in the production of 15 to 20 new proteins, from which lysozyme, cecropin and attacin have been purified.

The lysozyme gene and protein was obtained from Hyalophora-derived plasmid pBR322, provided by Kleanthis Xanthopoulos. The lysozyme gene was removed from the plasmid pBR322 by digestion with the enzyme Pst I. The resultant fragment was purified and treated with the Bal 31 enzyme to remove the 3' poly dG tail. Then the adapter shown as follows:

```
GTTTCATGAAACAGATCTGTCGACAGATCTGTTTCATGAAAC
CAAAGTACTTTGTCTAGACAGCTGTCTAGACAAAGTACTTTG
``` was ligated to the fragment after digestion with enzyme Xmn I. Then the fragment is digested with Sal I and cloned into the plasmid pBR322. The lysozyme gene was rescued by digestion with enzyme Bgl II and inserted into the plant vector pMON237.

The lysozyme gene coding for antibacterial proteins has been identified and contains the following nucleotide sequence:

```
AGATCTGTTTCATG AAA CGT TTC ACG AGA TGC GGG
TTA GTG CAG GAG CTT AGG AGA CGA GGC TTC GAT GAA ACT TTG ATG AGT AAC TGG
GTC TGC CTT GTC GAG AAC GAA AGC GGA CGG TTT ACC GAT AAA ATC GGT AAA GTT
AAC AAG AAC GGA TCT CGA GAC TAC GGC CTC TTC CAG ATC AAT GAC AAA TAC TGG
TGC AGT AAG GGA TCC ACT CCT GGA AAG GAT TGC AAC GTG ACT TGT AAT CAG CTA
CTG ACT GAC GAC ATT AGC GTG GCA GCT ACG TGC GCG AAG AAG ATT TAC AAA CGC
CAC AAG TTT GAC GCT TGG TAC GGA TGG AAA AAT CAC TGT CAA CAT GGA CTG CCA
GAT ATT AGC GAC TGT TAG AGACGACTTATTATAGCCTTC GTTTCATGAAAC
AGATCT.
```

This lysozyme gene produces an accompanying protein or polypeptide which has the amino acid sequence:

Lys Arg Phe Thr Arg Cys Gly
Leu Val Gln Glu Leu Arg Arg Arg Gly Phe Asp Glu Thr Leu Met Ser Asn Trp
Val Cys Leu Val Glu Asn Glu Ser Gly Arg Phe Thr Asp Lys Ile Gly Lys Val
Asn Lys Asn Gly Ser Arg Asp Tyr Gly Leu Phe Gln Ile Asn Asp Lys Tyr Trp
Cys Ser Lys Gly Ser Thr Pro Gly Lys Asp Cys Asn Val Thr Cys Asn Gln Leu
Leu Thr Asp Asp Ile Ser Val Ala Ala Thr Cys Ala Lys Lys Ile Tyr Lys Arg
His Lys Phe Asp Ala Trp Tyr Gly Trp Lys Asn His Cys Gln His Gly Leu Pro
Asp Ile Ser Asp Cys.

In a somewhat similar manner, the attacin gene and its accompanying protein, obtained as a part of the plasmid pBR322 from Kleanthis Xanthopoulos, were removed, provided with appropriate start and stop amino acids and inserted into a plant vector for inclusion into a suitable host for growth and testing for antibacterial properties in plant cells. The attacin gene was removed from pBR322 by digestion with the enzyme Pst I, according to conventional procedures. The resultant plasmid fragment was purified and digested with FnuDII and Dra I. The adapter oligonucleotide CGTCCATGGACGAGATCTGTCGACAGATCTCGTCCATGGACG
GCAGGTACCTGCTCTAGACAGCTGTCTAGAGCAGGTACCTGC was joined to the fragment by ligation. Then the adapter-containing fragment was digested with Sal I and cloned into plasmid pBR322. The full length attacin gene was then obtained from pBR322 by digestion with Bgl II and inserted into the plant vector pMON237 and had the start methionine at the amino terminus end. The plant vector pMON237 containing the antibacterial attacin gene confers this antibacterial property on plants produced from plant cells having the pMON237 inserted.

The attacin gene coding for antibacterial protein has been identified and contains the following nucleotide sequence:

AGATCTCGTCCATG
GAC GCG CAC GGA GCC CTT ACG CTC AAC TCC GAT GGT ACC TCT GGT GCT GTG GTT
AAA GTA CCC TTT CGT GGT AAC GAC AAG AAT ATA GTA AGC GCT ATC GGT TCC GTA
GAC TTA ACT GAT AGG CAG AAA CTA GGC GCT GCA ACC GCT GGA GTG GCA CTG GAT
AAT ATA AAC GGT CAC GGA CTA AGT CTC ACG GAT ACA CAC ATC CCC GGG TTC GGA
GAC AAG ATG ACA GCA GCC GGC AAA GTG AAT GTC TTC CAC AAT GAT AAC CAC GAC
ATC ACA GCG AAG GCT TTC GCC ACC AGA AAC ATG CCG GAT ATT GCT AAT GTA CCT
AAT TTC AAC ACT GTC GGT GGC GGA ATA GAC TAT ATG TTC AAA GAT AAG ATT GGT
GCA TCT GCG AGC GCC GCT CAC ACG GAC TTT ATC AAT CGC AAC GAC TAC TCT CTT
GAC GGG AAA CTG AAC CTC TTC AAG ACT CCT GAT ACC TCG ATT GAT TTC AAC GCC
GGT TTC AAG AAG TTC GAT ACA CCT TTC ATG AAG TCC TCT TGG GAG CCT AAC TTC
GGA TTC TCA CTT TCT AAA TAT TTC TGA TTA GTATTTTAATTTTAATTCTATATATATAAA
TTTAGATGTATATGTATATATATATATTTTTTTTTATTAATATGATATCACTAAATGTATTTACTCCTTC
GATTATTATTACTTTTTTTGTTTCGTCCATGGACGAGATCT.

This attacin gene produces an accompanying protein or polypeptide having the amino acid sequence as follows:

Asp Ala His Gly Ala Leu Thr Leu Asn Ser Asp Gly Thr Ser Gly Ala Val Val
Lys Val Pro Phe Ala Gly Asn Asp Lys Asn Ile Val Ser Ala Ile Gly Ser Val
Asp Leu Thr Asp Arg Gln Lys Leu Gly Ala Ala Thr Ala Gly Val Ala Leu Asp
Asn Ile Asn Gly His Gly Leu Ser Leu Thr Asp Thr His Ile Pro Gly Phe Gly
Asp Lys Met Thr Ala Ala Gly Lys Val Asn Val Phe His Asn Asp Asn His Asp
Ile Thr Ala Lys Ala Phe Ala Thr Arg Asn Met Pro Asp Ile Ala Asn Val Pro
Asn Phe Asn Thr Val Gly Gly Gly Ile Asp Tyr Met Phe Lys Asp Lys Ile Gly
Ala Ser Ala Ser Ala Ala His Thr Asp Phe Ile Asn Arg Asn Asp Tyr Ser Leu
Asp Gly Lys Leu Asn Leu Phe Lys Thr Pro Asp Thr Ser Ile Asp Phe Asn Ala
Gly Phe Lys Lys Phe Asp Thr Pro Phe Met Lys Ser Ser Trp Glu Pro Asn Phe
Phe Ser Leu Ser Lys Tyr Phe.

Further, and similarly, the antibacterial protein producing cecropin gene, obtained in plasmid pBR322 received from Kleanthis Xanthopoulos was first cut with restriction enzymes Pst I and HinPII to provide a plasmid fragment pCPFL1. The resulting 260 base pair fragment was purified and treated with T4 DNA polymerase to fill in the HinPII site. The resultant fragment was then treated with T4 DNA ligase and the synthetic adapter C3, which is identified as follows:

CT AGCAT AAAGAT CT GACGT CAGAT CT TT AT CCT AG
GAT CGT AT TT CT AGACT GCAGT CT AGAAAT AGGAT C, was joined to the fragment. The new gene fragment was then ligated to pBR322 which had been cleaved with restriction enzymes XmnI and AatII. Clones containing the correct ampicillin sensitive genotype were selected, cut with XmnI and ligated with a synthetic adaptor identified as C5, which has the following nucleotide sequence:

CT TT CCAT TT CAT GGT AGAT CT ACCAT GAAAT GGAAAG
GAAAGGT AAAGT ACCAT CT AGAT GGT ACT TT ACCT TT C

The resultant fragment was retransformed with E. Coli. The cecropin gene is rescued from E. Coli by digestion with Bgl II and inserted into the plant vector pMON237. Thus, the cecropin gene is regenerated without its leader peptide and with an appropriate start methionine at the amino terminus end and the correct translational termination (stop) signal at the carboxy terminus end.

The cecropin gene has been identified and has the following nucleotide sequence:

cecropin proteins, respectively. These novel microbes are available for reproduction and maintenance and will be preserved by the inventor at Louisiana State University, Baton Rouge, Louisiana, until such time as deposit in a commercial depository is required in the event of allowance of the present application. In view of the present discoveries and inventions, another feature of this invention is a composition comprising a plasmid contained in a microbe which contains a DNA sequence which codes for a polypeptide derived from the humoral response to bacterial infection of the Hyalophora. Particularly, the present invention includes a composition in which the microbe is *Agrobaeterium tumefaciens*. More particularly, the composition of this invention includes such a microbe in which the polypeptide is selected from lysozyme, attacin, cecropin and a mixture thereof.

The method of inhibiting fungi includes the selection, cloning and insertion of genes encoding for antifungal compounds into an appropriate plant vector. Certain naturally occurring bacteria produce toxins for fungi. Such bacteria retain gene(s) which encode for the production of these antifungal compounds. The DNA separated from these antifungal compound producing bacteria are isolated, shotgun cloned into a lambda vector and subsequently used to transfect E. Coli. In addition, the same DNA can be shotgun cloned into Pseudomonas directly using the Pseudomonas vectors pWS3 and pWS6 described by Wyerneke et al, Gene 38 (1985) 73–84. The resultant transformants are plated and oversprayed with the indicator single cell eukaryote Rhodotorula. This powerful selection tool locates the DNA (genes) encoding for the antifungal toxin compounds and characterizes them sufficiently to allow for their expression in a plant by suitable plant vectors in the manner previously described. Insertion of the antifungal compounds as genes or AGAT CT ACCAT GAAAT GGAAAGT CT T C AAGAAA
ATT GAA AAA ATG GGT CGC AAC ATT CGA AAC CGT ATT GTC AAG GCT GGA
CCA GCG ATC GCG GTT TTA GGC GAA GCC AAA GCG CTA GGA T AA AGAT CT.

This cecropin gene produces an accompanying protein or polypeptide having an antibacterial amino acid sequence as follows:

DNA encoding therefor provides plant species having antifungal properties.

Lys Trp Lys Val Phe Lys Lys
Ile Glu Lys Met Gly Arg Asn Ile Arg Asn Gly Ile Val Lys Ala Gly
Pro Ala Ile Ala Val Leu Gly Glu Ala Lys Ala Leu Gly.

The *Agrobacterium tumefaciens* microbes containing the insect produced antibacterial proteins produced according to the method of the present invention have been given the designations pAT-LYS, pAT-ATN and pAT-CN for those which contain genes encoding for lysozyme, attacin and In much the same manner a species providing a chitinase enzyme is selected for identification, cloning, insertion into a plant vector and production of a plant producing the chitinase enzyme. It has been found that certain species of the bacterial genus Vibrio produce a very active chitinase enzyme. Thus another aspect of this invention provides a method for inhibiting insect infestation and insect damage to plants by providing a chitinase enzyme producing plant. The DNA or gene encoding for production of the chitinase enzyme can be cut out of the Vibrio bacteria DNA with digestion by the restriction enzyme Hind III. A DNA sequence analysis can be employed to determine the appropriate start and stop positions of the gene. Further cloning is required to implant the desired gene into the plant genome as described previously for the antibacterial encoding genes inserted into plant vectors.

The method for inhibiting viruses and viroids includes the provision of an antisense or complementary oligonucleotide which inhibits or prevents the replication of the virus or viroid or which inhibits the translation of the virus. In Vitro procedures utilizing a 41 base DNA oligonucleotide having the sequence:

```
GATCTCCACGGTTGTGGCCATATAATCATCGTGTTTTTCAA
``` effectively blocked 98% of the translation of a virus genome. This procedure was carried out by hybridizing the DNA to the virus in an 8 microliter reaction mixture containing 20 mM Hepes, pH 7.6, 0.1M NaCl and 1 mM ETDA. RNA concentration of the virus was 0.5 mg/ml and the DNA was added in a five-fold molar excess. In general, the reaction mixtures were heated at 70° C. for 10 minutes followed by incubation at 45° C. for 3 hours. The process of determining viral RNA translation is in a cell-free protein synthesis regime, such as in RNA rabbit reticulocyte lysate system described by Shih et al at Proceedings of the National Academy of Science of the U.S.A., 75, 5807–5811 (1978) and in the Journal of Virology, 30, 472–480 (1979), both of which are incorporated by reference as if fully set forth. As a result of the hybridization, viral translation was effectively blocked.

In the case of viroids, replication was prevented in the potato spindle tuber viroid (PSTV) by hybridization of synthetic DNA fragments to the PSTV in the central conserved region which appears to be present in all known viroids and is presumed to be important for replication. The synthetic DNA fragments have the oligonucleotide sequence and identification as follows:

```
GATCT AGGGAT CCCCGGGGAAACCT  PSTV1
GATCT AGGTTT CCCCGGGGAT CCCT  PSTV2
```

This hybridization was carried out by annealing the various oligonucleotide fractions to purified, infectious PSTV RNA. The sample mixture was heated to 90° C. for 5 minutes and then allowed to cool slowly to room temperature. These mixtures were then innoculated onto PSTV sensitive tomato plants and symptoms were allowed to develop. The results are shown in the Table below.

Table of Molar Ratio of Compositions Innoculated in Tomato Plants

| Innocula | Molar Ratio | Infected Tomato Plants (#infected/#innoculated) |
|---|---|---|
| PSTV + PSTV1 | 1:1 | 0/4 |
| PSTV + PSTV1 | 10:1 | 0/4 |
| PSTV + PSTV1 | 1:10 | 0/4 |
| PSTV + PSTV2 | 1:1 | 0/4 |
| PSTV + PSTV2 | 10:1 | 2/4 |
| PSTV + PSTV2 | 1:10 | 0/4 |
| PSTV + PSTVf* | 1:1 | 1/4 |
| PSTV + PSTVf | 10:1 | 0/4 |
| PSTV + PSTVf | 1:10 | 0/4 |
| PSTV alone |  | 3/5 |

*PSTVf is a full length DNA of PSTV.

When hybridization occurs, the further replication of the PSTV molecule was blocked.

The synthetic DNA transcription blocking for viroids and synthetic DNA translation blocking for viruses are inserted into a plant vector to produce plants which are not susceptible to the viroids and viruses described.

Having described the invention, one skilled in the art will be aware of variations and changes therein which are within the scope and spirit of the present invention. Therefore, it is desired that the invention be limited only by the lawful scope of the following claims.

We claim:

1. A method of inhibiting a pathogenic fungal or bacterial plant condition, said method comprising: incorporating into a dicotyledonous plant genome one or more genes which encode for a polypeptide inhibitor or inhibitor precursor of said pathogenic condition, which inhibitor or inhibitor precursor is selected from the group consisting of attacins and cecropins.

2. The method of claim 1 wherein said incorporating is by infecting said plant with an Agrobacterium microbe containing said gene or genes.

3. The method of claim 2 wherein said Agrobacterium is *Agrobacterium tumefaciens*.

4. The method of claim 1 wherein said polypeptide is cecropin.

5. The method of claim 1 wherein said polypeptide is attacin.

6. The method of claim 1 further comprising incorporating into the genome of said plant a gene which encodes for lysozyme.

7. A plant produced according the method of claim 1 or claim 6.

* * * * *